US010575495B2

(12) United States Patent
Coiro et al.

(10) Patent No.: US 10,575,495 B2
(45) Date of Patent: Mar. 3, 2020

(54) METHOD AND SYSTEM FOR MONITORING AIR FLOW IMPURITY

(71) Applicant: ALLENTOWN INC., Allentown, NJ (US)

(72) Inventors: John M. Coiro, Allentown, NJ (US); Brian M. Bilecki, Allentown, NJ (US); Thomas P. Schupsky, Allentown, NJ (US)

(73) Assignee: ALLENTOWN, LLC, Allentown, NJ (US)

(*) Notice: Subject to any disclaimer, the term of this patent is extended or adjusted under 35 U.S.C. 154(b) by 929 days.

(21) Appl. No.: 15/169,704

(22) Filed: May 31, 2016

(65) Prior Publication Data

US 2016/0353704 A1    Dec. 8, 2016

Related U.S. Application Data

(60) Provisional application No. 62/169,438, filed on Jun. 1, 2015, provisional application No. 62/280,057, filed on Jan. 18, 2016.

(51) Int. Cl.
| | | |
|---|---|---|
| *A01K 1/00* | (2006.01) | |
| *A01K 1/03* | (2006.01) | |
| *G01N 1/22* | (2006.01) | |
| *B01D 46/00* | (2006.01) | |

(52) U.S. Cl.
CPC ............ *A01K 1/0047* (2013.01); *A01K 1/031* (2013.01); *G01N 1/2205* (2013.01); *G01N 1/2247* (2013.01); *B01D 46/0032* (2013.01); *G01N 2001/2223* (2013.01)

(58) Field of Classification Search
CPC ........ A01K 1/0047; A01K 1/031; A01K 31/06; A01K 1/03
USPC ................. 119/419, 500, 420, 493, 417, 502
See application file for complete search history.

(56) References Cited

U.S. PATENT DOCUMENTS

| | | | | |
|---|---|---|---|---|
| 3,428,026 A | * | 2/1969 | Sohmers ................ | A01K 1/033 119/452 |
| 4,095,559 A | * | 6/1978 | Griffith ................ | A01K 1/0107 119/163 |
| 4,546,727 A | * | 10/1985 | Andersen ............. | A01K 1/0107 119/165 |
| 4,862,831 A | * | 9/1989 | Graham ................ | A01K 1/035 119/419 |
| 5,134,972 A | * | 8/1992 | Compagnucci ...... | A01K 1/0107 119/165 |
| 5,307,757 A | | 5/1994 | Coiro, Sr. et al. | |
| 5,307,761 A | * | 5/1994 | Berger, III ........... | A01K 1/0107 119/165 |

(Continued)

FOREIGN PATENT DOCUMENTS

KR    200439455    3/2007

*Primary Examiner* — Yvonne R Abbott-Lewis
(74) *Attorney, Agent, or Firm* — Porzio Bromberg & Newman P.C.

(57) ABSTRACT

A method and system for monitoring conditions of a rack of animal cages. An animal caging system including a plurality of animal cages removably connected to an exhaust. Collection media is removably mounted in an exhaust plenum of the rack using a holder. Exhaust air dust clings to the collection media as exhaust from the animal cages flows along the length of the collection media. A door to the exhaust plenum can be opened and the collection media can be removed from the holder.

27 Claims, 16 Drawing Sheets

(56) References Cited

U.S. PATENT DOCUMENTS

| | | | | | |
|---|---|---|---|---|---|
| 5,315,964 | A | * | 5/1994 | Mimms | A01K 1/0107 119/165 |
| 5,477,810 | A | * | 12/1995 | Wilkison, III | A01K 1/031 119/459 |
| 5,564,364 | A | * | 10/1996 | Kovacs | A01K 1/0107 119/163 |
| 5,655,478 | A | * | 8/1997 | Kiera | A01K 1/0107 119/165 |
| 5,778,822 | A | * | 7/1998 | Giffin | A01K 1/0047 119/165 |
| 6,036,737 | A | * | 3/2000 | Smith | B01D 46/42 454/56 |
| 6,123,048 | A | * | 9/2000 | Alkire | A01K 1/0107 119/163 |
| 6,176,201 | B1 | * | 1/2001 | Fields | A01K 1/0107 119/163 |
| 6,227,147 | B1 | * | 5/2001 | Ball | A01K 1/033 119/484 |
| 6,308,660 | B1 | * | 10/2001 | Coiro, Sr. | A01K 1/031 119/419 |
| 6,341,579 | B1 | * | 1/2002 | Alkire | A01K 1/0107 119/165 |
| 6,782,845 | B1 | * | 8/2004 | Schmidt | A01K 1/031 119/419 |
| 7,363,879 | B2 | * | 4/2008 | Bonner | A01K 1/0035 119/417 |
| 8,297,230 | B2 | * | 10/2012 | Ferrer | A01K 1/0047 119/165 |
| 8,485,131 | B2 | * | 7/2013 | Veness | A01K 1/0107 119/165 |
| 2005/0205017 | A1 | * | 9/2005 | Irwin | A01K 1/031 119/455 |

* cited by examiner

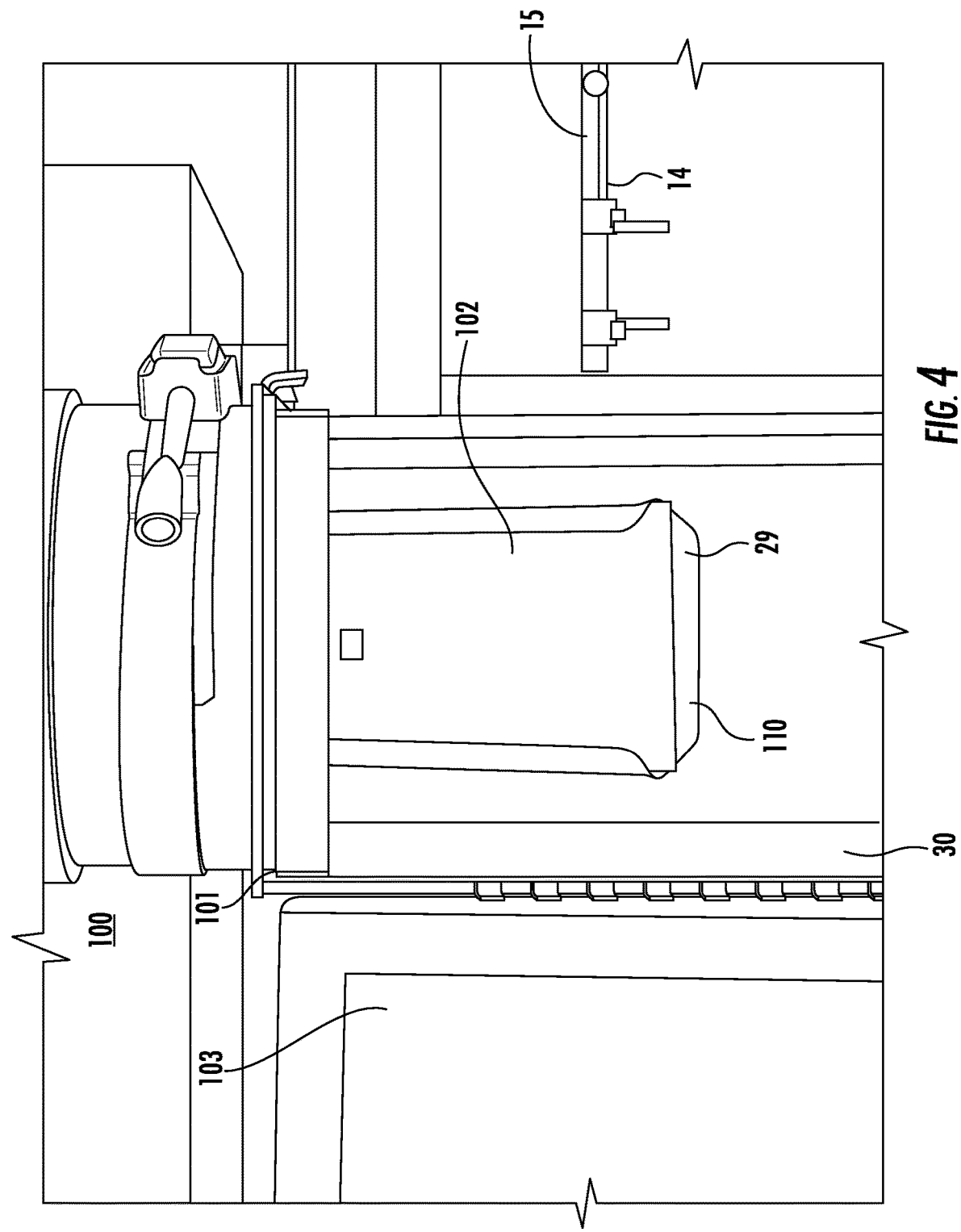

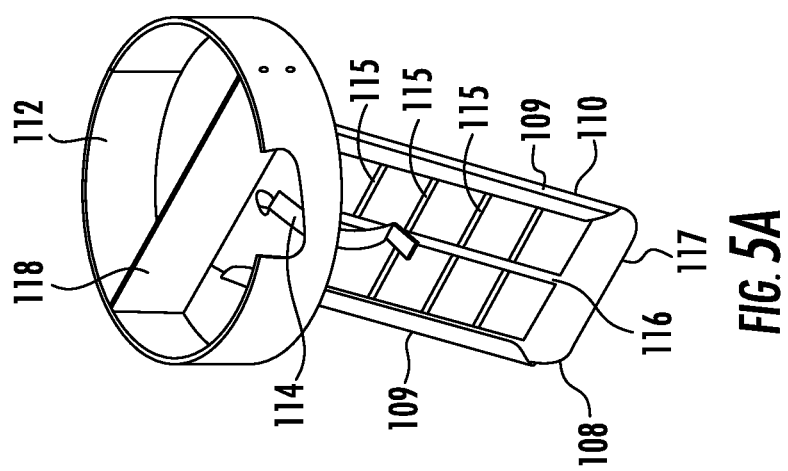
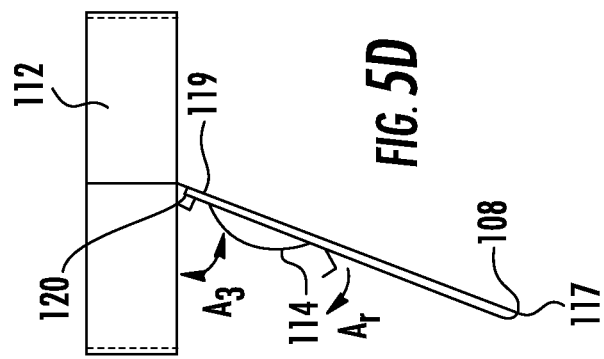
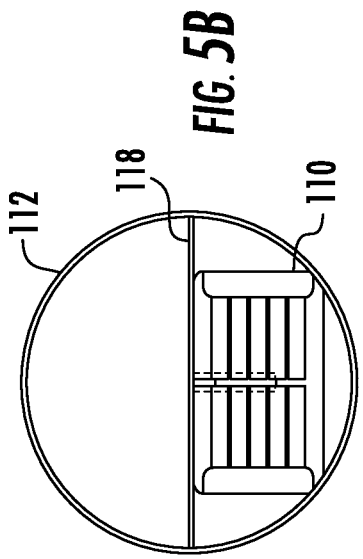
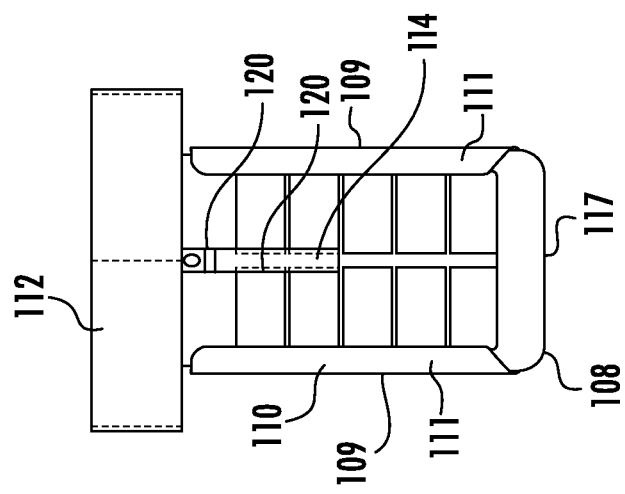
FIG. 5A
FIG. 5D
FIG. 5B
FIG. 5C

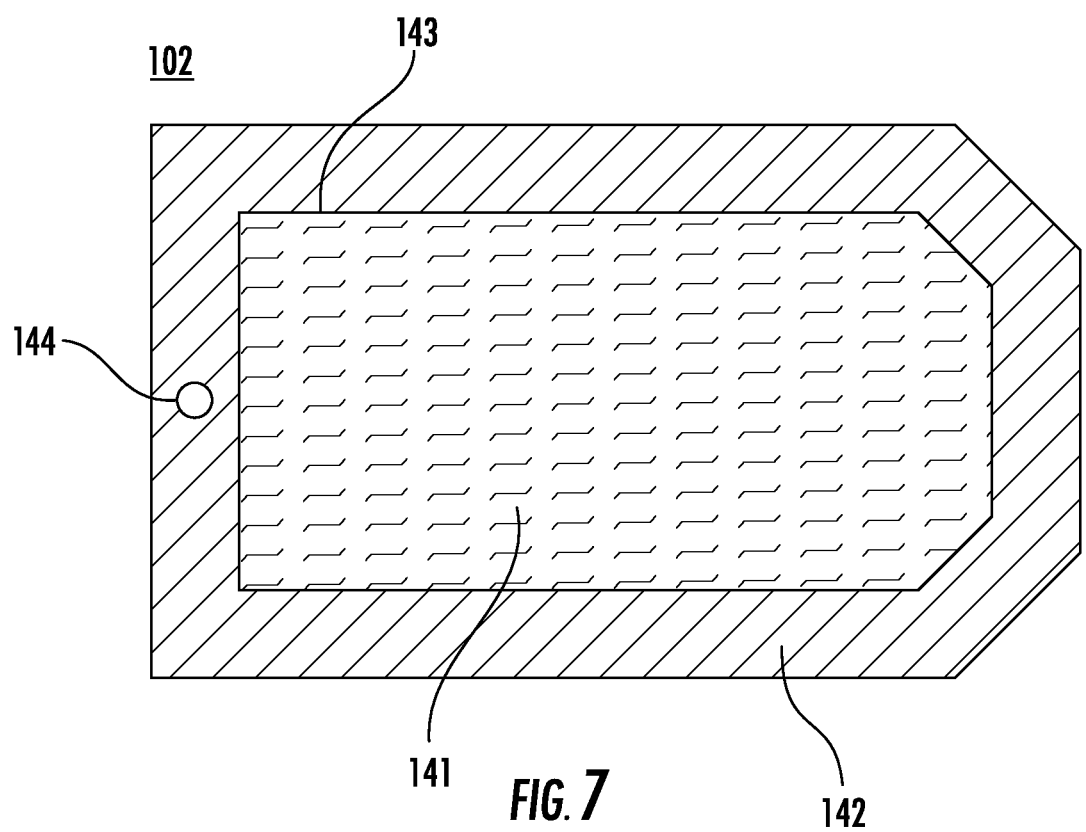

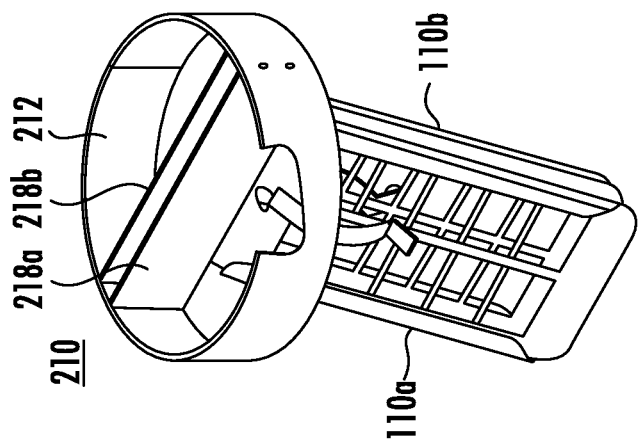
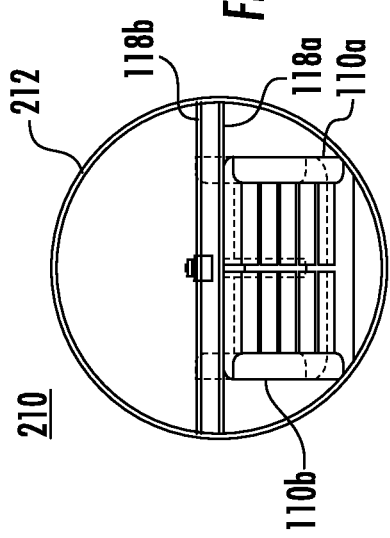
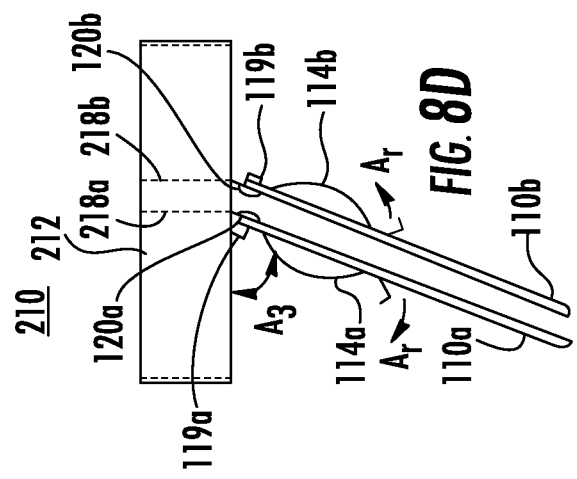
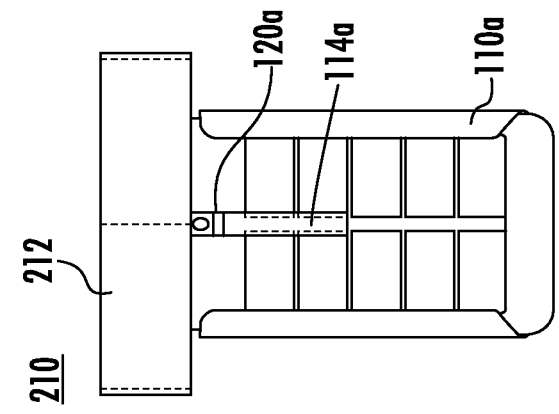

METHOD AND SYSTEM FOR MONITORING AIR FLOW IMPURITY

BACKGROUND OF THE INVENTION

Field of the Invention

The present invention relates to a system for monitoring conditions of a rack of animal cages and in particular to monitoring rodent and other laboratory animal pathogens within the entirety of a ventilated caging system for the purposes of monitoring animal health.

Description of Related Art

Systems for providing air and removing exhaust from racks containing animal cages are known. U.S. Pat. No. 5,307,757 describes a ventilated animal rack and animal cage system including a forced air system in which positive air is supplied by an air inlet manifold. Air is removed from the cage by negative air pressure to an exhaust manifold. The exhausted air is treated with a laboratory air treatment system or portable HEPA filtered exhaust unit and is released to the atmosphere.

U.S. Pat. No. 6,308,660 describes an animal caging system including a self-sealing animal cage removably connected to an air supply and an exhaust. The self-sealing animal cage is supported by a rack. The self-sealing animal cage is sealed by an air inlet connection and an air outlet connection to the air supply and the exhaust connection. After the cages are removed from the air supply and the exhaust, the air inlet connection and the exhaust connection seals the cage to prevent air from entering or exiting the cage.

The air supply and exhaust are provided with an air delivery and exhaust apparatus side mounted to the rack. The air delivery and exhaust apparatus is integrated with high efficiency particulate air (HEPA) filters. The air delivery and exhaust apparatus operates in a positive pressure mode for pushing air into the cage or in a negative mode for withdrawing air from the cage. Air from the environment is HEPA filtered and is used as supply air in the air delivery apparatus and exhaust air from the exhaust apparatus is HEPA filtered before being emitted into the environment. The animal caging system provides isolation of the self-sealing animal cage and provides containment of airborne pathogens within the caging system.

Animals contained in the animal cages can have exposure to viruses, parasites and bacteria. Sentinel animals that have been placed in a cage environment have been removed from the environment and monitored to find out if rodent pathogen or other harmful organisms are present in that environment.

It is desirable to provide a method and system for monitoring conditions of the rack of animal cages, not requiring the use of sentinel animals.

SUMMARY OF THE INVENTION

The present invention relates to a method and system for monitoring conditions of a rack of animal cages. The present invention comprises an animal caging system including a plurality of animal cages removably connected to an air supply and an exhaust. The animal cages are supported by a rack.

Air including dust carrying rodent pathogen nucleic acid can be removed from the rack of animal cages into a vertical exhaust plenum. A collection media is removably mounted in a terminus of the exhaust plenum of the rack. In one embodiment, the collection media is mounted in a ring mounted collection media holder at an angle within a vertical exhaust plenum. Exhaust air passes along the length of the collection media. Exhaust air dust clings to the collection media. The collection media holder does not reduce airflow within the vertical exhaust plenum. Additionally, there should be no deterioration of pressure within the cage(s) due to reduced airflow caused by a restriction in the vertical exhaust plenum.

The collection media can be removed and placed into a sample container. The sample container can be forwarded to a facility for testing of the collection media. For example, the collection media can be tested for rodent pathogens.

In one embodiment, a plurality of collection media can be removably retained in a holder in contact with exhaust from the animal cages. The additional collection media can be used as backup in the event that a first sample is lost in shipping or can be retained for retesting as a second sample, for example if an unexpected result was determined from the first tested sample. Alternatively, the collection media can comprise a perforated media to allow the media to be separated. In one application, one side of the media can be submitted for sampling and the other side of the media can be retained as a backup.

The invention will be more fully described by reference to the following drawings.

BRIEF DESCRIPTION OF THE DRAWINGS

FIG. 3 illustrates a side view of the air delivery and exhaust apparatus in combination with.

FIG. 4 illustrates a front view of an exhaust plenum including an exhaust plenum door in an open position.

FIG. 5A is a perspective view of a collection media holder of the present invention.

FIG. 5B is a top view of the collection media holder shown in FIG. 5A.

FIG. 5C is a front view of the collection media holder shown in FIG. 5A.

FIG. 5D is a side view of the collection media holder shown in FIG. 5A.

FIG. 7 is a schematic diagram of a collection media.

FIG. 8A is a perspective view of an alternate embodiment of a collection media holder of the present invention.

FIG. 8B is a top view of the collection media holder shown in FIG. 8A.

FIG. 8C is a front view of the collection media holder shown in FIG. 8A.

FIG. 8D is a side view of the collection media holder shown in FIG. 8A.

DETAILED DESCRIPTION

Figure 1C:
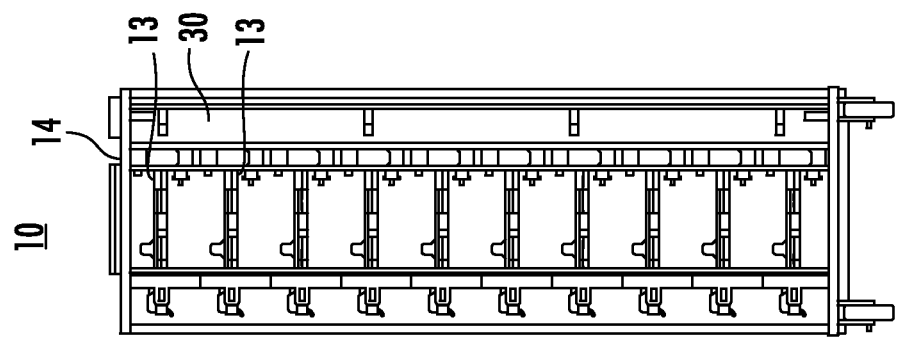
FIG. 1C illustrates an end cross-section view of the end opposite to the end shown in FIG. 1B.

Reference will now be made in greater detail to a preferred embodiment of the invention, an example of which is illustrated in the accompanying drawings. Wherever possible, the same reference numerals will be used throughout the drawings and the description to refer to the same or like parts.

FIGS. 1A-1D illustrate a system for monitoring animal health via exhaust air dust carried by the air flow 10 in accordance with the teachings of the present invention. Individual animal cages 12 are supported on at least one shelf, platform or suspended runner system 13 on rows 15 of rack 14. Example animal cage racks are manufactured by Allentown, Inc. as Nexgen, Micro-Vent and PNC.

Figure 1A:
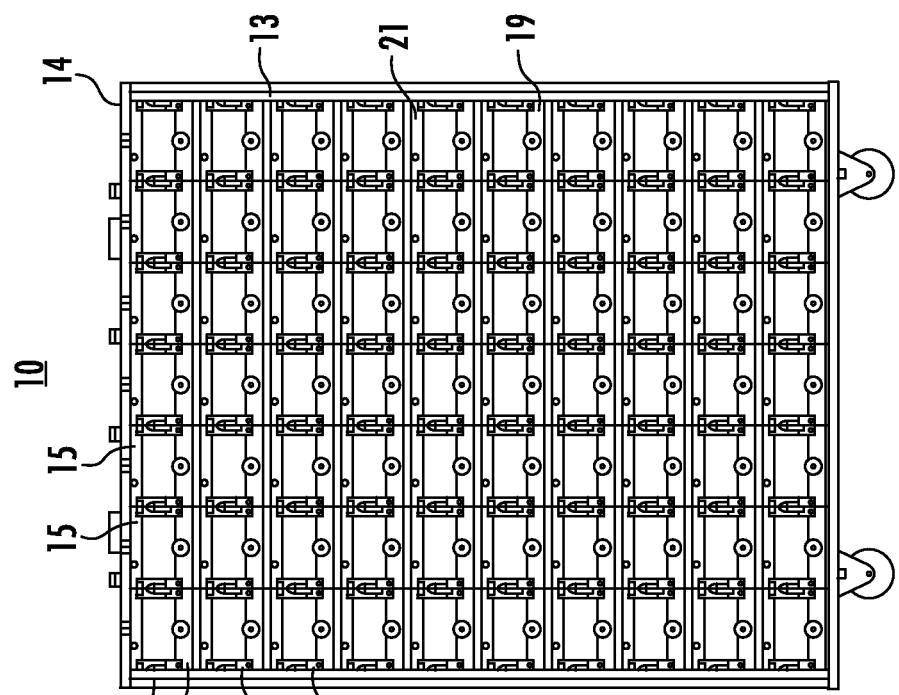
FIG. 1A illustrates a side elevational view of a system for monitoring air flow impurity animal cage system in accordance with the teachings of the present invention.
Figure 1B:
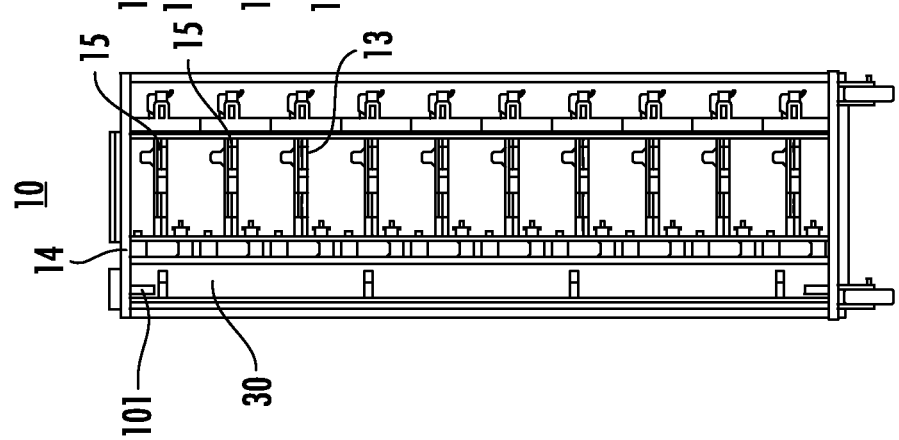
FIG. 1B illustrates an end cross-section view of the system shown in FIG. 1A.
Figure 1D:
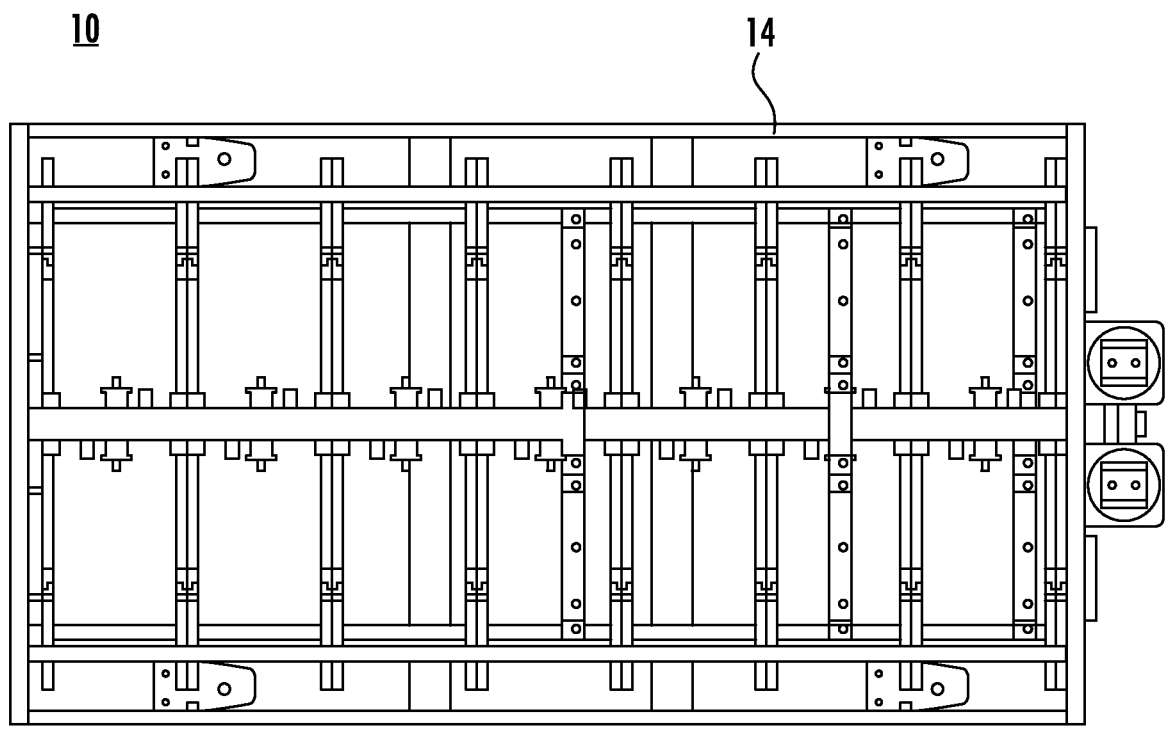
FIG. 1D illustrates a top view of the system shown in FIG. 1A.
Figure 2A:
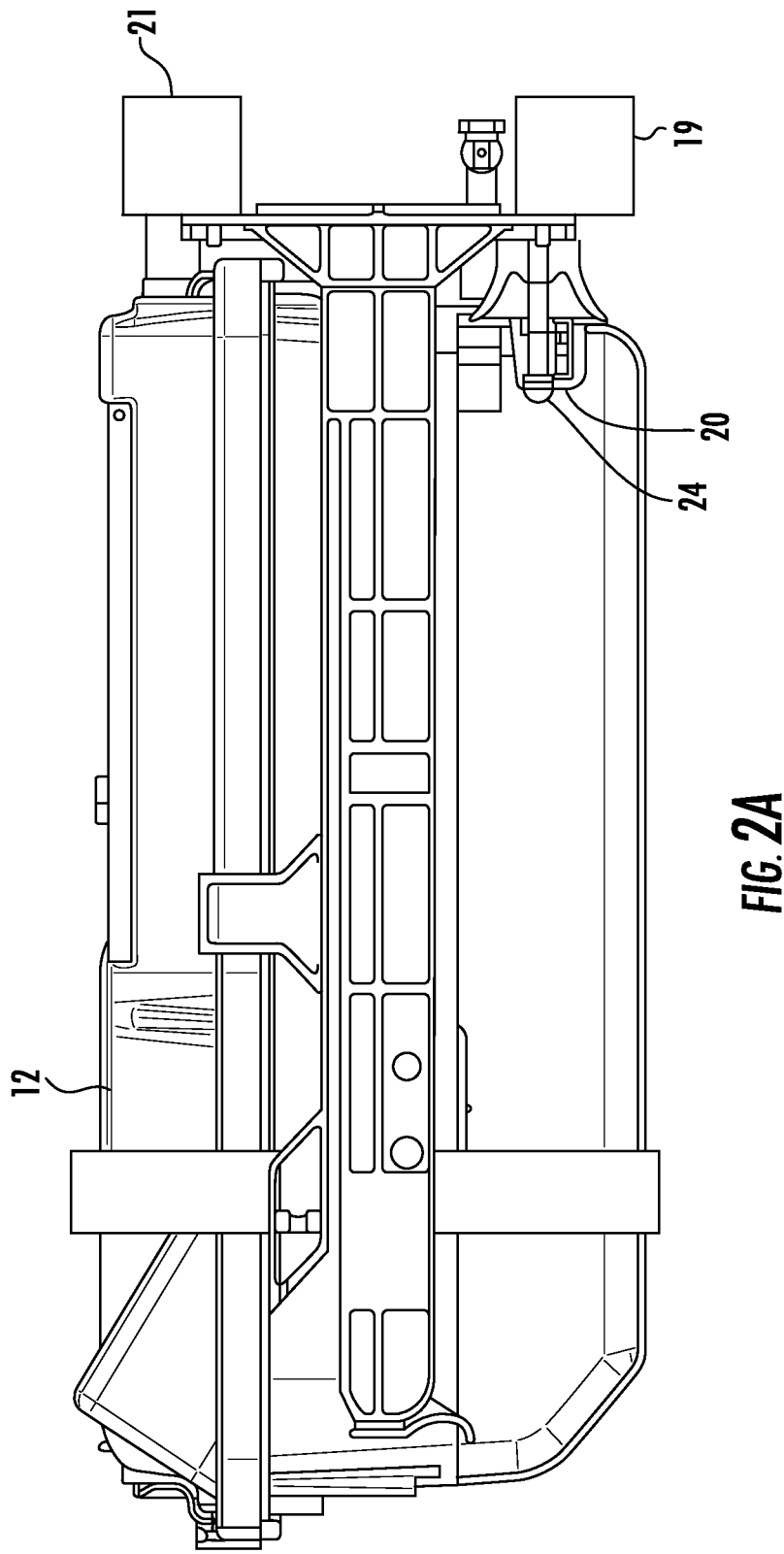
FIG. 2A illustrates a side perspective view of an animal cage and connection to an air supply plenum and an exhaust plenum.
Figure 2B:
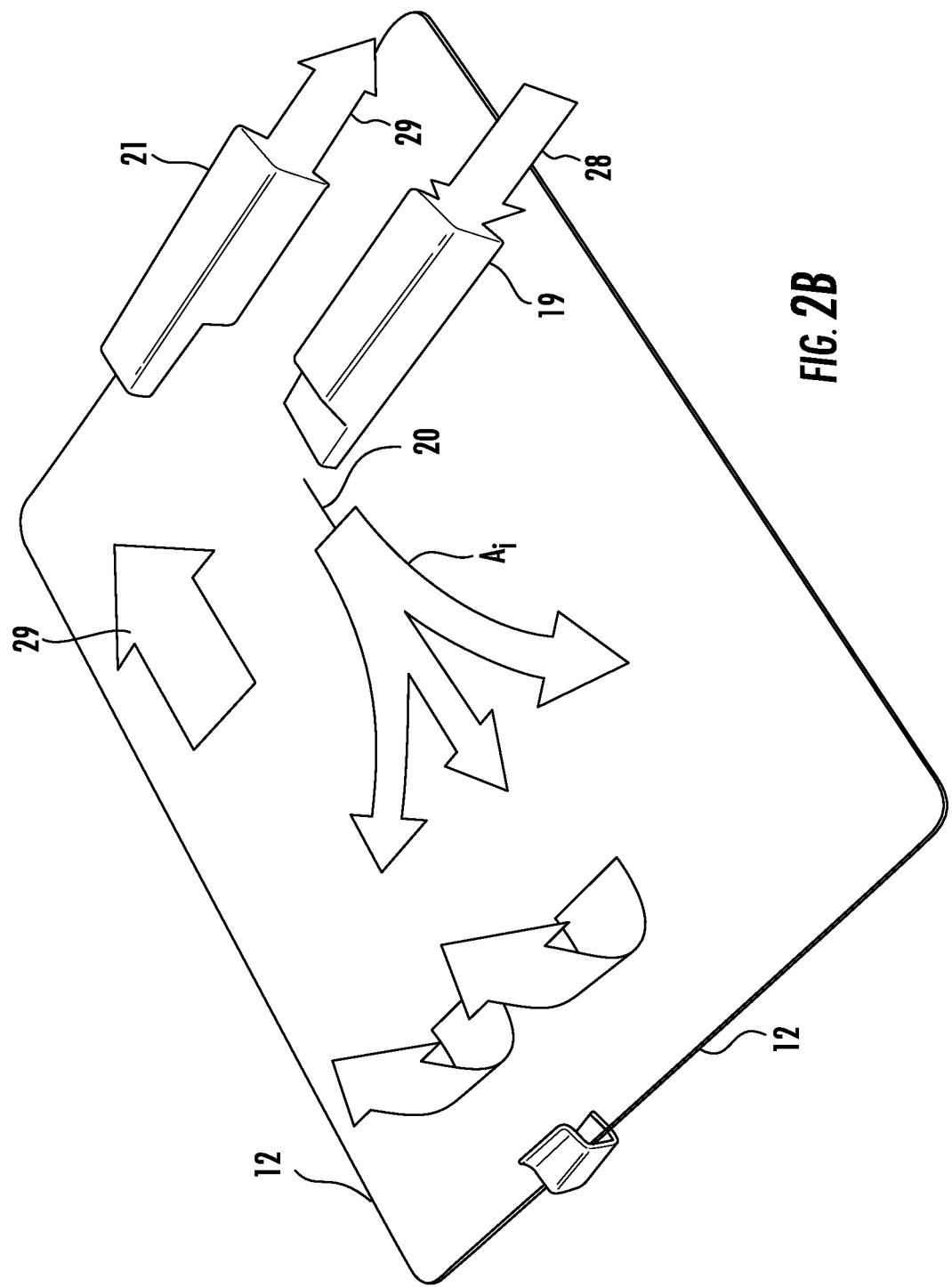
FIG. 2B illustrates a perspective view of air flow in the animal cage.
Figure 3:
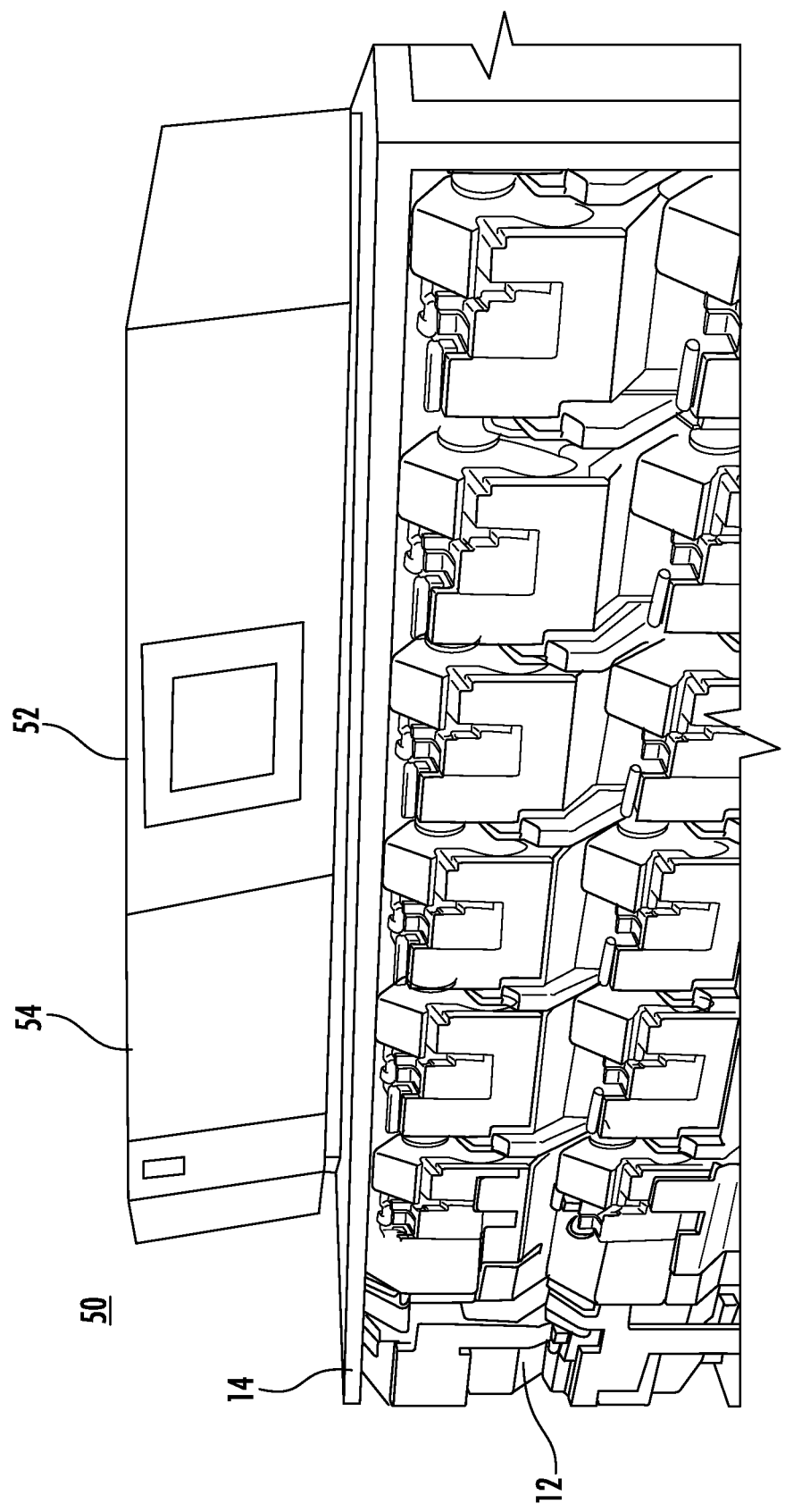

An example animal cage 12 is shown in FIGS. 2A-2B. Nozzle 20 includes at least one air opening 22 formed in end 24 of nozzle 20 for emitting air 28 into animal cage 12 in the direction of arrow $A_i$ as shown in FIG. 2B. 1 Air supply plenum 19 provides air 28 to nozzle 20. Air 28 circulates within the animal cage 12 and exits animal cage 12 in the direction of arrow $A_o$ as exhaust 29 through exhaust plenum 21. Exhaust plenum 21 connects to exhaust plenum 30, as shown in FIG. 1A. In this embodiment, exhaust plenum 21 is positioned in a substantially horizontal direction and exhaust plenum 30 is positioned in a substantially vertical direction. It will be appreciated that exhaust plenum 21 and exhaust plenum 30 can be positioned in alternative directions or integral with one another.

Air delivery and exhaust apparatus 50 comprises at least one rack mounted supply blower 52 and at least one rack mounted exhaust blower 54 for supplying air to rack 14 and removing exhaust from rack 14 Alternatively air delivery and exhaust apparatus can supply and exhaust air via wall mounted or tower blower ventilation system, such as one manufactured by Allentown Inc. as an EcoFlo Rack, Eco-Flow Tower. Alternatively air delivery and exhaust apparatus can be supplied by an above ceiling or remotely mounted air supply device such as one manufactured by Allentown Inc. Eco Flow Interstitial Blower while using the facility available exhaust system to exhaust the rack such as demonstrated in the Allentown Inc system FIAS (Facility Integrated Airflow Solutions).

Collection system 100 is removably mounted at terminus 101 in exhaust plenum 30 as shown in FIG. 4. This location allows for cumulated sample collection of all animal cages 12 contained in all rows 15 of rack 14. It will be appreciated that collection system 100 can be used with any animal cage rack system including an exhaust plenum. In one embodiment, collection system 100 includes collection media 102 mounted in collection media holder 110. Exhaust plenum door 103 to exhaust plenum 30 can be opened and collection media 102 can be removed from collection media holder 110.

An example collection media holder 110 is shown in FIGS. 5A-5D. Ring mounting 112 can be attached to collection media holder 110. For example, ring mounting 112 can be welded to collection media holder 110. Collection media holder 110 can be formed of a plurality of horizontal members 115 extending from vertical member 116 to form a grid pattern. Vertical lip 111 can be positioned at outer edges 109 of collection media holder 110. The grid pattern retains collection media 102 and provides sufficient contact of exhaust 29 with collection media 102 as shown in FIG. 4. Ring mounting 112 can be slip fit into terminus 101 at vertical exhaust plenum 30.

Collection media holder 110 can be angled at an Angle $A_3$ within exhaust plenum 30 to provide improved contact of exhaust 29 with collection media 102 as shown in FIG. 5D. For example, Angle $A_3$ can be in the range of about 15 to about 25 degrees from vertical. Preferably, Angle $A_3$ is about 20 degrees.

Horizontal lip 117 at end 108 of collection media holder 110 can provide turbulence to air flowing over collection media holder 110 to enhance flow of exhaust 29 into collection media 102. Collection media 102 can be used to capture exhaust air dust captured from exhaust 29 from cage 12 as exhaust 29 passes along the length of collection media 102.

Spring clip 114 can be attached to center mount 118 of ring mounting 112 by inserting end 119 of spring clip 114 through slot 120 in center mount 118. Spring clip 114 provides clamping of collection media 102. Spring clip 114 can be moved in the direction of arrow $A_r$ for removing collection media 102 from collection media holder 110.

Collection media holder 110 can be formed of metal or plastic. In one embodiment, collection media holder 110 is formed of stainless steel.

Figure 6A:
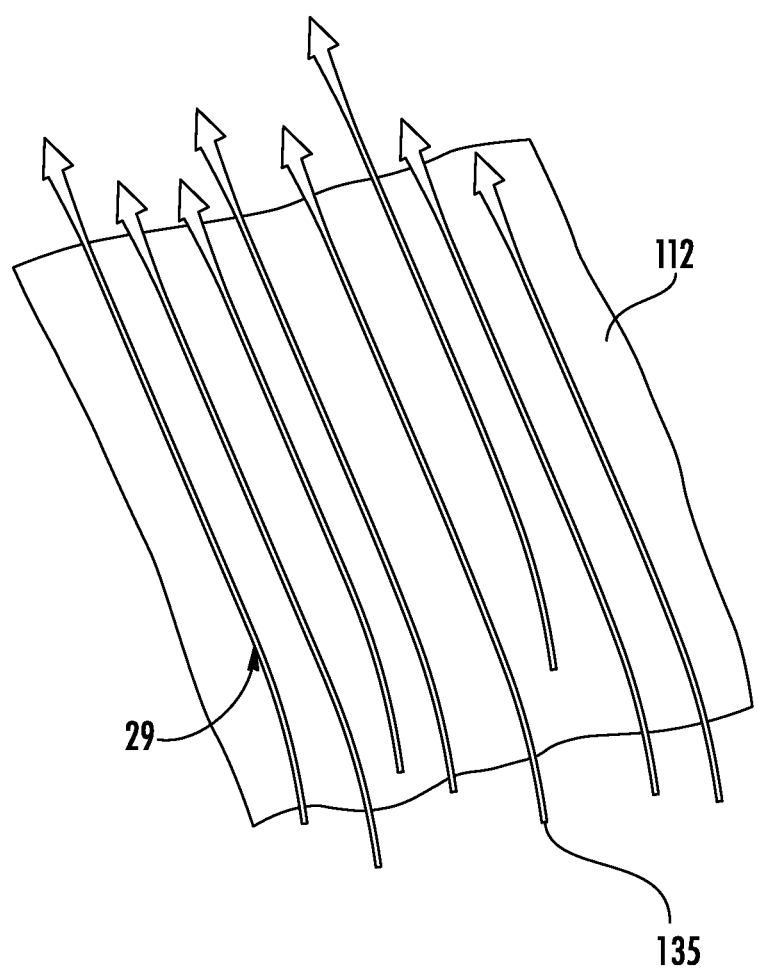
FIG. 6A is a schematic diagram of air flow into the collection media holder.
Figure 6B:
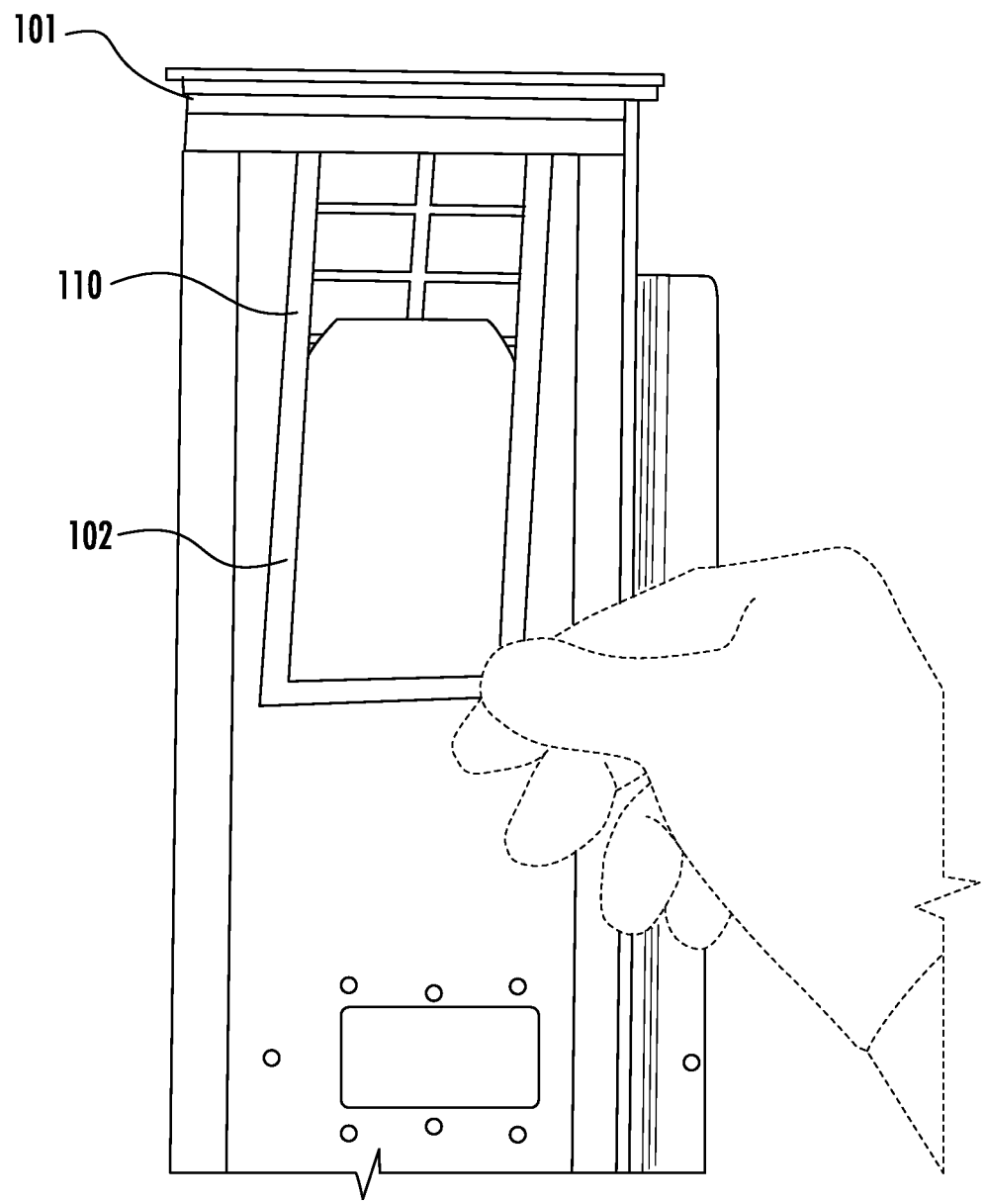
FIG. 6B is a schematic diagram of removal of a collection media from the collection media holder.
Figures 6C, 6D:
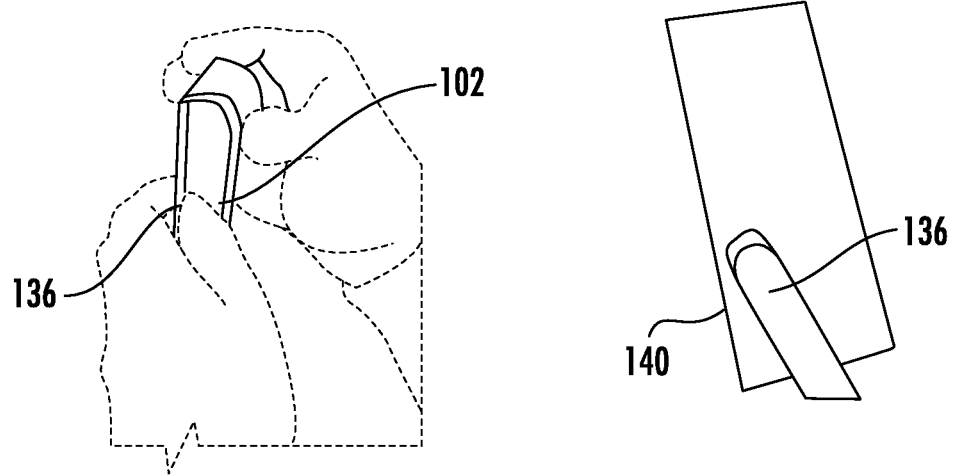
FIG. 6C is a schematic diagram of placing of the collection media in a container.
FIG. 6D is a schematic diagram of placing of the container in a shipping package.

During use of ventilated animal cage with EAD collection system 10, particulate 135 in exhaust 29 are entrapped in collection media 102 as shown in FIG. 6A. Collection media 102 can be removed from collection media holder 110 as shown in FIG. 6B. Removed collection media 102 can be placed into sample container 136 as shown in FIG. 6C. Sample container 136 can be placed in mailing package 140 to be forwarded to a facility for testing of collection media 102 as shown in FIG. 6D. For example, collection media 102 can be tested for rodent pathogens.

FIG. 7 is a schematic diagram of an embodiment of collection media 102. Collection media 102 comprises media 141 coupled to frame 142. Frame 142 extends around outer edge 143 of collection media 102. In one embodiment, primary media 141 is heat sealed to frame 142 for aiding in creating a more rigid structure to aid in handling, inserting and removing the collection media. Frame 142 is marked with indicia 144. Indicia 144 can be for example a dot or notch. Indicia 144 can be used to identify direction of insertion of collection media 102 into collection media holder 110 as well as in container 136.

Media 141 can be constructed of an electrostatically charged and controlled gradient structure consisting of thermally bonded or alternatively blended bicomponent polypropylene/polyethylene fibers, spun bond, continuous filament and attracts both positively and negatively charged particles with low moisture regain. Alternatively this can consist of one or more of the following materials, polyester or polyolefine fibers in the bonded or bicomponent structure. Media 141 can prevent fibers from swelling due to moisture absorbed from the air stream. In one embodiment, media 141 is white. Media 141 can carry a varying MERV (Minimum Efficiency Rating Value), rating between about 6 and about 10. Suitable media 141 can have a rating of MERV 8 (Minimum Efficiency Rating Value), a basis weight of 2.00 oz/yd$^2$, thickness 64 mils, Frazier Air Permeability 490 cfm/ft$^2$. In other embodiments of media 141 the polypropylene fibers can be substituted by polyolefin fibers.

Frame 142 can comprise collection media containing 100% polyester fibers. In one embodiment, frame 142 comprises a white spun collection media with a basis weight of 8.0 oz/yd$^2$, nominal thickness of 23 mils. strip tensile MD: 125 lbf/0.6 in. Frame 142 can be constructed of any of a number of similar media that can be heat sealed to media 141 and has a basis weight between 6 and 10 and could be manufactured of various synthetic fibers. Collection media 102 can be supplied as non-sterile or sterile in some embodiments.

FIGS. 8A-8D show an alternate embodiment of collection media holder 210. Ring mounting 212 can be attached to a plurality of collection media holders 110a,110b. Ring mounting 212 can be slip fit into terminus 101 at vertical exhaust plenum 30.

Each of collection media holders 110a, 110b can be angled at an Angle $A_3$ within exhaust plenum 30 to provide improved contact of exhaust 29 with collection media 102 as shown in FIG. 8D. Collection media 102 in each of collection media holders 110a, 110b can be used to capture exhaust air dust captured from exhaust 29 from cage 12 as exhaust 29 passes along the length of collection media 102.

Spring clip 114a can attach collection media holder 110a to center mount 218a of ring mounting 212 by inserting end 219a of spring clip 114a through slot 120a in center mount 218a. Spring clip 114b can attach collection media holder 110b to center mount 218b of ring mounting 212 by inserting end 219b of spring clip 114b through slot 120b in center mount 218b. Spring clips 114a, 114b provide clamping of collection media 102 as shown in FIG. 8D. Spring clips 114a, 114b can be moved in the direction of arrow $A_r$ for respectively removing collection media 102 from collection media holders 110a, 110b.

Figure 9:
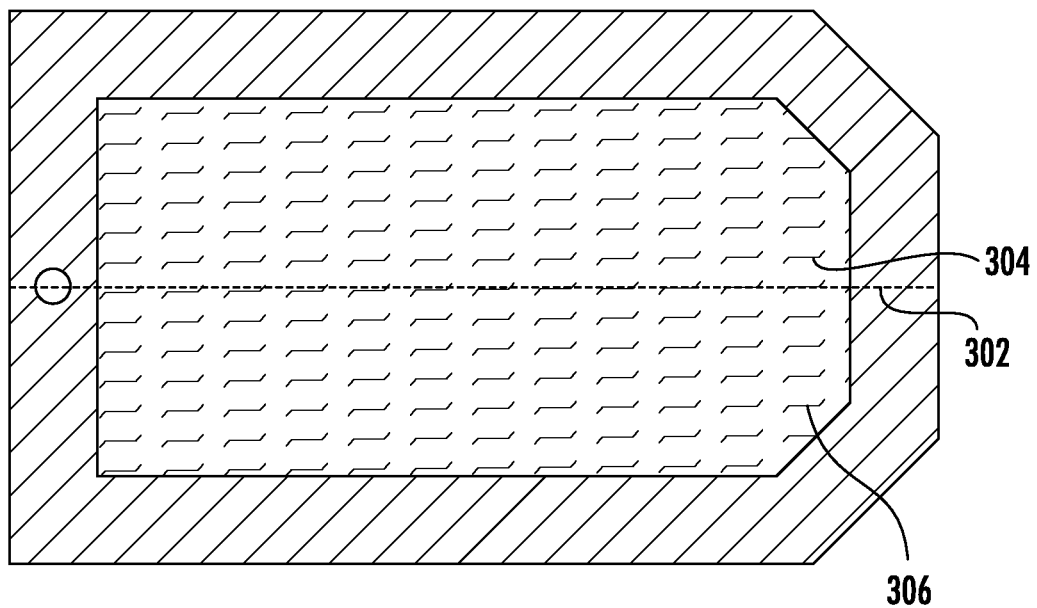
FIG. 9 is a schematic view of an alternate embodiment of a collection media.

FIG. 9 shows an alternative embodiment of collection media 102 including perforation 302. Perforation 302 is positioned between side 304 and side 306 of collection media 102. Perforation 302 can be separated to separate side 304 of collection media 102 from side 306 of collection media 102.

Figure 10:
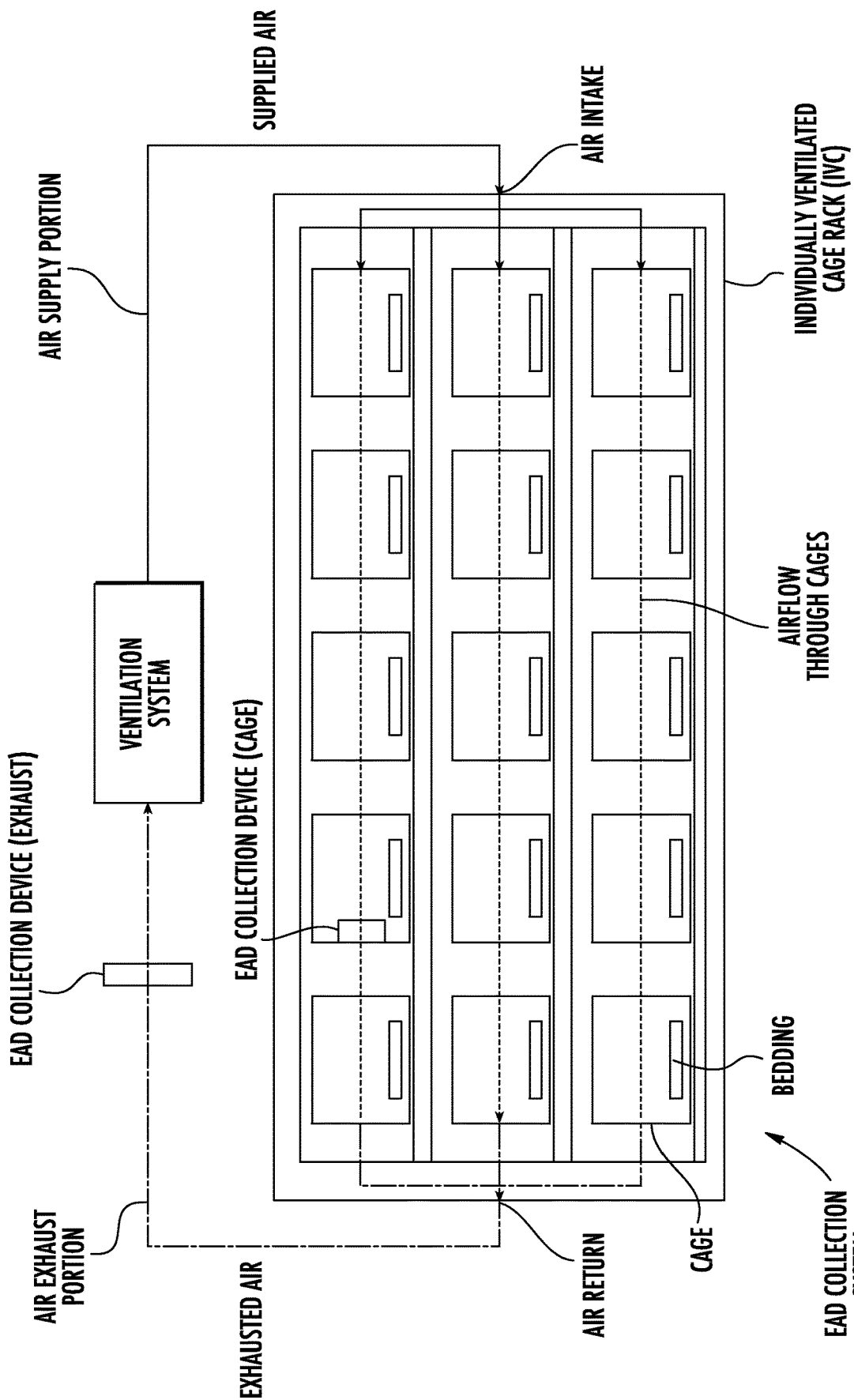
FIG. 10 is a schematic illustrations of a system for collecting Environmental Air Dust (EAD) from an Individually Ventilated Cage Rack System (IVC) environment.

FIG. 10 is a schematic illustration of an embodiment of a system for collecting environmental air dust (EAD) from a micro-isolator caging environment. For the purpose of discussion, embodiments of the disclosure will be discussed in the context of an individually ventilated cage rack (IVC). However, any micro-isolator caging may be employed without limit. The collection system includes the IVC, a plurality of cages, and a plurality of EAD collection devices. The IVC includes a plurality of cages for housing animals (e.g., rodents). In certain embodiments, the cages may be arranged in an array having generally aligned rows and columns. The ventilation system supplies a flow of air (e.g., sterile air) to the IVC and returns a flow of air exhaust from the IVC (e.g., air including dust and attached pathogen molecules) via an airflow pathway. The supplied air is routed through an air supply portion of the airflow pathway and may include plenums on the rack that distribute the supplied air to different locations on the rack (e.g., different rows and/or columns). The exhausted air is routed through an air exhaust portion of the airflow pathway and may include plenums on the rack that collect the exhausted air from different locations on the rack (e.g., different rows). The airflow pathway through the cages (i.e., from the air supply portion to the air exhaust portion) is routed through one or more plenums in fluid communication with the air supply portion, the air exhaust portion, and a plurality of cages on the rack. In use, the flow of air directed through the IVC is sufficient to transport at least a portion of EAD from respective cage locations into the air exhaust portion of the airflow pathway. The embodiment of FIG. 10 is illustrated with a closed ventilation system, where air exhaust is reconditioned and reused as the air supply. However, in alternative embodiments, not shown, the ventilation system may be an open system, where the air supply is not provided from reconditioned air exhaust but instead from a separate source.

The plurality of EAD collection devices are designed for capturing at least a portion of EAD transported by the flow of air while allowing at least a portion of the flow of air to move unimpeded there-through. Captured EAD may be retained on the surface of the EAD collection device, the bulk of the EAD collection device, and/or within a dedicated containment chamber, based on the configuration of the EAD collection device. Example collection devices may include, but are not limited to, mechanical filters, chemical filters, wet scrubbers, electrostatic filters, and other filtering devices suitable for removing dust from air, without limit.

Each EAD collection device may be independently selected to capture EAD having a size (e.g., diameter, cross-sectional area, or other selected dimension) approximately greater than a selected value. In other embodiments, the collection device may be graded, with spatial regions of the collection device selected to capture EAD of different sizes. Such zones may vary continuously or discontinuously within the spatial extent of the collection device. In certain embodiments, EAD collection devices may be selected to capture dust particles having a size ranging from about 0.1 nm to about 10 mm. In further embodiments, EAD collection devices may possess efficiency between about 5% to about 40% at about the selected size. In certain embodiments, the efficiency of EAD collection devices may be approximately 30% at about the selected size.

The position of the collection device may be varied, depending upon the configuration of the IVC. For example, as illustrated in FIG. 10, one or more EAD collection devices may be positioned in the flow exhaust air within the air exhaust portion, illustrated as "EAD Collection Device (Exhaust). In alternative embodiments, one or more EAD collection devices may be positioned on or within one or more selected cages, illustrated as "EAD Collection Device (Cage). In further embodiments, at least one EAD collection devices may be positioned on each of the exhaust and the cage.

In the embodiment of FIG. 10, supplied air is received from a ventilation system. One or more EAD collection devices can be positioned in the exhaust air flow.

Figure 11:
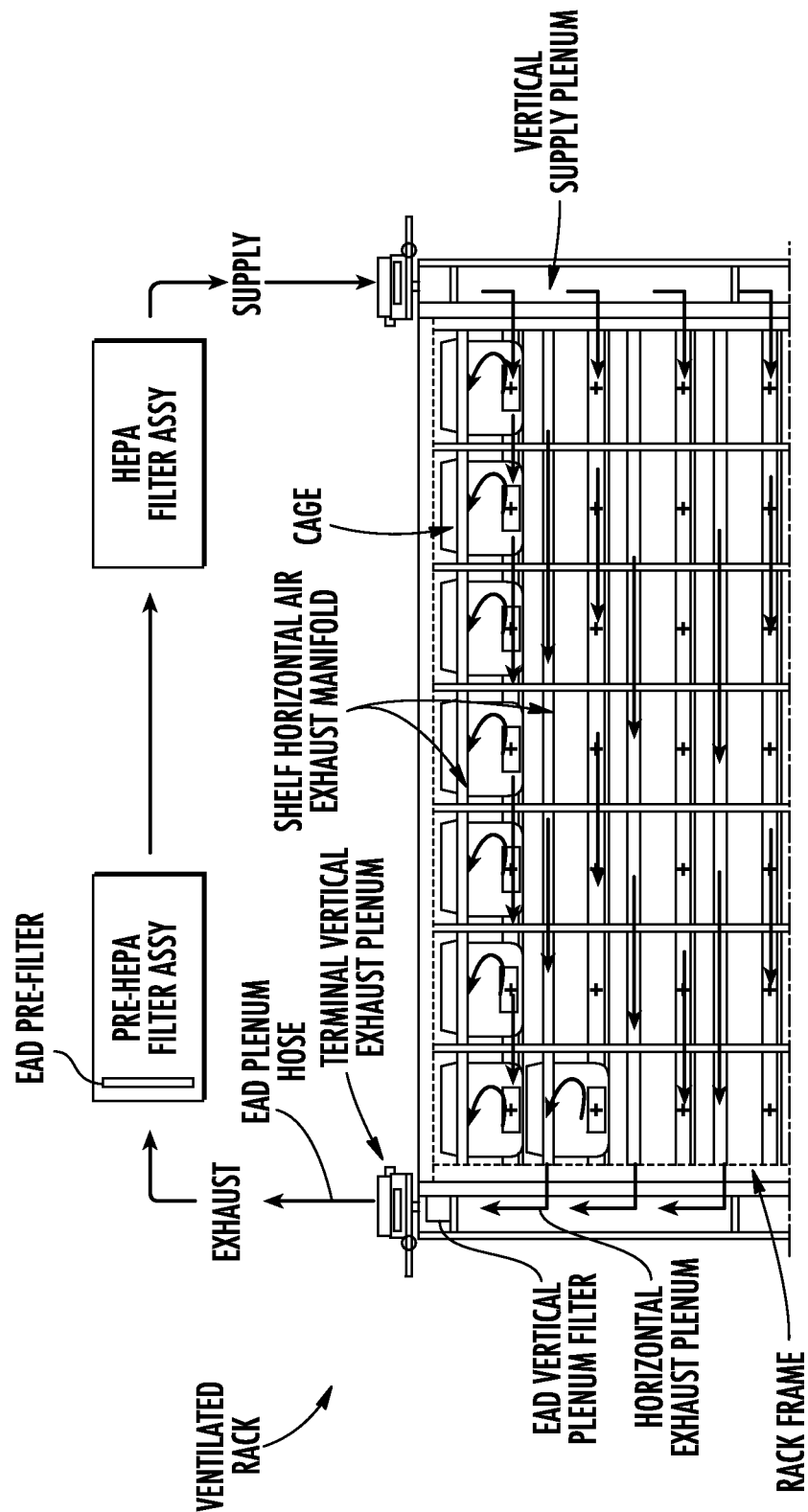
FIG. 11 is a schematic illustrations of embodiments of an EAD collection system utilized for testing comparative examples.
Figure 12B:
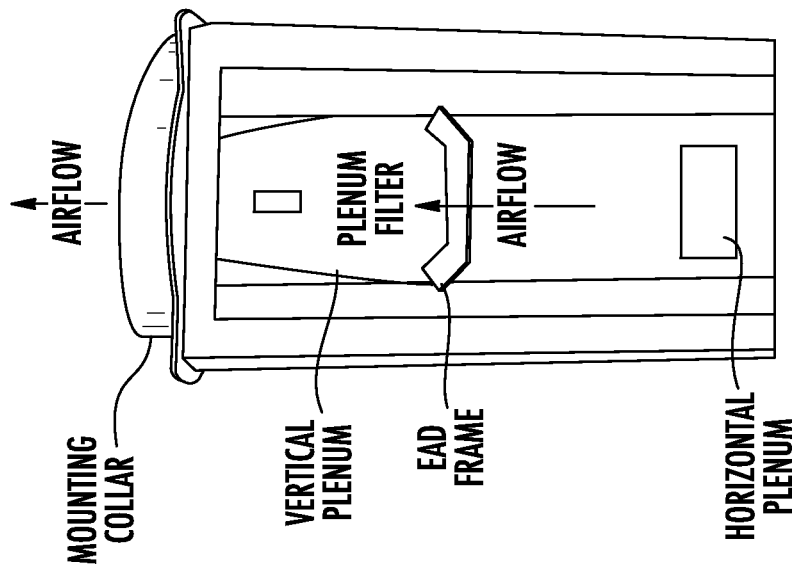
FIGS. 12A-12B are photographs illustrating placement of embodiments of EAD collection devices employed with the EAD collection system of FIG. 11 for testing comparative examples; (A) A frame for support of an EAD collection device; (B) EAD filter positioned in vertical plenum.
Figure 12A:
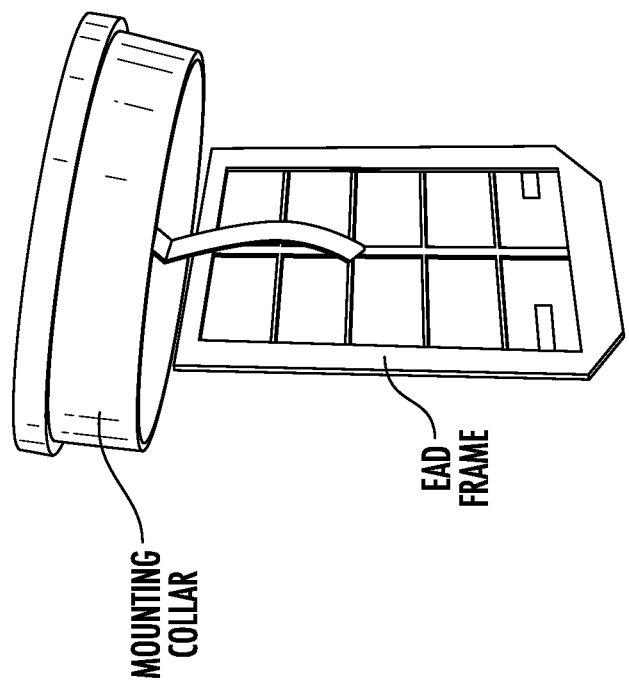

With reference to FIGS. 11 and 12A-12B, collection of EAD samples by in-line EAD collection device will now be discussed. FIG. 11 presents a schematic illustration of an embodiment of a ventilated rack employed in the instant examples. A supply of sterile air is supplied to a first end of the rack including a generally vertical supply plenum. The supply plenum directs the supply air through the cages of the rack via a generally elongated horizontal plenum to an opposing second end of the rack including a generally vertical exhaust plenum. EAD and pathogens attached thereto are carried by the air flow from their respective cages out of the rack. The ventilation system included a pre-HEPA filter assembly and a HEPA filter assembly. The pre-HEPA filter assembly received air from the air exhaust. Air flowing through the pre-HEPA filter assembly was directed into the HEPA filter assembly.

A EAD collection devices was positioned within the airflow path. As illustrated in FIGS. 11 and 12A-12B, the EAD collection device was a physical filter suspended near the top of the vertical exhaust plenum. A frame (FIG. 11) was secured to a collar adapted for mounting adjacent a top mouth of the vertical exhaust plenum. So positioned, the EAD collector was suspended within the plenum at a position intersecting the expected exhaust air flow pathway. As each of the EAD collection device is positioned within the exhaust air flow that has passed through the extent of the rack, any EAD collected thereon is expected to be representative of the rack as a whole.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A collection system for monitoring animal health, the collection system adapted to be mounted in an exhaust plenum of an animal cage system comprising:
   a collection media holder, the collection media holder configured for removably retaining collection media,
   the animal cage system includes at least one animal cage,
   a rack for supporting the at least one animal cage and
   an air supply supplying air to the at least one animal cage and the exhaust plenum receives exhaust from the at least one animal cage,
   wherein the collection media holder is configured to be mounted in the exhaust plenum of the animal cage system and air from the air supply passes through said at least one cage to exit the cage as the exhaust and the collection media captures environmental air dust and pathogens within the exhaust received in the exhaust plenum.

2. The collection system of claim 1 wherein the collection system is adapted to be mounted at a terminus of the exhaust plenum.

3. The collection system of claim 1 wherein collection media holder is formed of a plurality of horizontal members extending from a vertical member to form a grid pattern, the grid pattern adapted to retain the collection media.

4. The collection system of claim 1 wherein the collection media holder includes a horizontal lip at a bottom portion of the collection media holder.

5. The collection system of claim 1 wherein the collection media holder includes a vertical lip at either side edge of said collection media holder.

6. The collection system of claim 1 wherein the collection media comprises a fiber material which electrostatically attracts positively and/or negatively charged particles.

7. The collection system of claim 6 wherein the fiber material comprises thermally spun bonded fibers.

8. The collection system of claim 6 wherein the fiber material is formed of one or more of polypropylene fibers, polyethylene fibers or polyolefin fibers.

9. The collection system of claim 6 further comprising a frame extending around edges of the collection media.

10. The collection system of claim 1 comprising a plurality of the collection media holders, each of the plurality of collection media holders adapted for retaining collection media.

11. The collection system of claim 1 wherein said exhaust plenum includes a door and the door is adapted to be opened to remove the collection media holder.

12. A collection system adapted to be mounted in an exhaust plenum of an animal cage system comprising:
    a collection media holder, the collection media holder adapted for removably retaining collection media and
    a ring mounting attached to the collection media holder.

13. The collection system of claim 12 wherein said ring mounting is adapted to fit into a terminus of the exhaust plenum.

14. The collection system of claim 12 wherein the collection media holder is adapted to be angled at an angle from the ring mounting.

15. The collection system of claim 14 wherein the angle from the ring mounting is in the range of about 15 to about 25 degrees.

16. The collection system of claim 12 wherein the ring mounting includes a center mount and a spring clip is coupled to the center mount.

17. The collection system of claim 16 wherein the spring clip is attached to the center mount of the ring mounting by inserting a first end of the spring clip through a slot in the center mount, the second end of the spring clip adapted to clamp the collection media.

18. A collection media holder adapted to be mounted in a vertical exhaust plenum of an animal cage system comprising:
    a collection media holder adapted for retaining a collection media,
    wherein the collection media holder comprises a frame, a collar being secured to the frame, the collar adapted for mounting adjacent a top mouth of the vertical exhaust plenum.

19. The collection media holder of claim 18 wherein the collection media holder is adapted to be mounted at a terminus of the vertical exhaust plenum.

20. The collection media holder of claim 18 wherein the frame is secured at an angle from the collar.

21. The collection system of claim 20 wherein the angle from the collar is in the range of about 15 to about 25 degrees.

22. The collection media holder of claim 18 wherein the frame has openings therein.

23. The collection media holder of claim 18 wherein the collar includes a center mount and a spring clip is coupled to the center mount, said spring clip adapted to attach the collection media to the frame.

24. The collection media holder of claim 18 wherein the animal cage system comprises at least one animal cage and further comprising:
    a rack for supporting the at least one animal cage; and
    an air supply supplying air to the at least one animal cage and the vertical exhaust plenum receives exhaust from the at least one animal cage,
    wherein the air from the air supply passes through the at least one cage to exit the cage as the exhaust and the collection media captures one or more materials within the exhaust.

25. A collection system adapted to be mounted in an exhaust plenum of an animal cage system comprising:
    a collection media holder, the collection media holder adapted for removably retaining collection media, and a frame extending around edges of the collection media, wherein the frame is heat sealed to the collection media.

26. A collection system adapted to be mounted in an exhaust plenum of an animal cage system comprising:
   a collection media holder, the collection media holder adapted for removably retaining collection media, and
   a frame extending around edges of the collection media, wherein the frame is formed of spun polyester fibers.

27. A collection system adapted to be mounted in an exhaust plenum of an animal cage system comprising:
   a collection media holder, the collection media holder adapted for removably retaining collection media, wherein the collection media holder comprises a first side and a second side and a perforation separates said first side from said second side.

\* \* \* \* \*